(12) United States Patent
Bradway (10) Patent No.: US 10,307,276 B2
(45) Date of Patent: Jun. 4, 2019

(54) PISTOL STENT DELIVERY DEVICE AND METHOD OF OPERATING SAME (71) Applicant: Cook Medical Technologies LLC, Bloomington, IN (US)

(72) Inventor: Ryan Bradway, Tacoma, WA (US)

(73) Assignee: Cook Medical Technologies LLC, Bloomington, IN (US)

( * ) Notice: Subject to any disclaimer, the term of this patent is extended or adjusted under 35 U.S.C. 154(b) by 114 days.

(21) Appl. No.: 15/483,428

(22) Filed: Apr. 10, 2017

(65) Prior Publication Data

US 2018/0014954 A1 Jan. 18, 2018

Related U.S. Application Data (60) Provisional application No. 62/363,557, filed on Jul. 18, 2016.

(51) Int. Cl.
A61F 2/95 (2013.01)
A61F 2/966 (2013.01)
A61F 2/844 (2013.01)

(52) U.S. Cl.
CPC .............. A61F 2/95 (2013.01); A61F 2/844 (2013.01); A61F 2/966 (2013.01);
(Continued)

(58) Field of Classification Search
CPC .. A61F 2002/011; A61F 2/2427; A61F 2/242; A61F 2/2433; A61F 2/2436;
(Continued)

(56) References Cited

U.S. PATENT DOCUMENTS 5,968,052 A 10/1999 Sullivan, III et al.
6,004,328 A 12/1999 Solar
(Continued)

FOREIGN PATENT DOCUMENTS

EP 2724695 4/2014
WO 9823241 6/1998
(Continued)

OTHER PUBLICATIONS

European Patent Office, European Search Report for Application No. 17181299.3, Published Nov. 23, 2017, Munich Germany.

Primary Examiner — Wade Miles
(74) Attorney, Agent, or Firm — Liell & McNeil (57) ABSTRACT The stent delivery device includes a pistol shaped handle with a barrel portion extending atop a grip portion. A trigger actuator is pivotably mounted to the pistol shaped handle and defines an angle with respect to the grip portion. A carrier is slidably mounted to the barrel portion of the pistol shaped handle. A mechanical linkage, which includes a roller clutch, interconnects the trigger actuator to the carrier. The angle is reduced responsive to pivoting the trigger actuator in an actuation direction toward the grip portion, and the angle is increased responsive to pivoting the trigger actuator in a re-set direction. The roller clutch is oriented in the mechanical linkage to rotate responsive to the trigger pivoting in the re-set direction, but the roller clutch is held against rotation responsive to pivoting the trigger in the actuation direction.

20 Claims, 6 Drawing Sheets (52) U.S. Cl.
CPC ............ *A61F 2002/9511* (2013.01); *A61F 2002/9517* (2013.01); *A61F 2002/9665* (2013.01)

(58) Field of Classification Search
CPC .. A61F 2/2439; A61F 2/95; A61F 2002/9505; A61F 2002/9511; A61F 2002/9517; A61F 2/954; A61F 2/958; A61F 2002/9583; A61F 2/962; A61F 2/966
See application file for complete search history.

(56) References Cited

U.S. PATENT DOCUMENTS

| | | | |
|---|---|---|---|
| 6,391,051 B2 | 5/2002 | Sullivan, III et al. | |
| 7,052,511 B2 | 5/2006 | Weldon et al. | |
| 7,819,882 B2 | 10/2010 | Rourke | |
| 8,292,939 B2 | 10/2012 | Yachia et al. | |
| 8,382,813 B2 | 2/2013 | Shumer | |
| 8,500,789 B2 | 8/2013 | Wuebbeling et al. | |
| 2004/0153137 A1* | 8/2004 | Gaschino | A61F 2/95 623/1.11 |
| 2005/0149159 A1* | 7/2005 | Andreas | A61F 2/95 623/1.11 |
| 2011/0282425 A1* | 11/2011 | Dwork | A61F 2/95 623/1.11 |
| 2012/0172963 A1 | 7/2012 | Ryan et al. | |
| 2013/0268049 A1* | 10/2013 | Munsinger | A61F 2/95 623/1.11 |
| 2015/0094794 A1 | 4/2015 | Cummins et al. | |
| 2016/0120678 A1 | 5/2016 | Green et al. | |
| 2018/0014954 A1* | 1/2018 | Bradway | A61F 2/844 |

FOREIGN PATENT DOCUMENTS

| | | |
|---|---|---|
| WO | 2008034793 | 3/2008 |
| WO | 20110081997 | 7/2011 |

* cited by examiner

PISTOL STENT DELIVERY DEVICE AND METHOD OF OPERATING SAME

TECHNICAL FIELD

The present disclosure relates generally to vascular intervention device delivery systems, and more particularly to a pistol shaped stent delivery device that utilizes a roller clutch in its mechanical linkage.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficulty maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control during the deployment because the force needed to deploy the stent decreases as the stent is deployed. If the user maintains the same high force during deployment, the stent may be deployed too fast for the user to control. Another potential problem relates to building up tension in the outer sheath prior to movement thereof during the deployment process. If the user pauses during the deployment and releases this built up tension, deployment errors can occur when the user resumes tension to again move the outer sheath to the deployment position fully uncovering the self expand stent.

The present disclosure is directed toward one or more of the problems set forth above.

SUMMARY OF THE DISCLOSURE

In one aspect, a stent delivery device includes a pistol shaped handle with a barrel portion extending atop a grip portion. A trigger actuator is pivotably mounted to the pistol shaped handle and defines an angle with respect to the grip portion. A carrier is slidably mounted to the barrel portion of the pistol shaped handle. A mechanical linkage, which includes a roller clutch, interconnects the trigger actuator to the carrier. The angle is reduced responsive to pivoting the trigger actuator in an actuation direction toward the grip portion, and the angle is increased responsive to pivoting the trigger actuator in a re-set direction. The roller clutch is oriented in the mechanical linkage to rotate responsive to the trigger pivoting in the re-set direction, but the roller clutch holds against rotation responsive to pivoting the trigger actuator in the actuation direction.

In another aspect, a method of operating a stent delivery device includes pivoting a trigger actuator of a pistol shaped handle toward a grip portion in an actuation direction. An analog mechanical linkage that interconnects the trigger actuator to a carrier moves responsive to moving the trigger actuator. The analog mechanical linkage includes a roller clutch. The carrier slides along a barrel portion of the pistol shaped handle responsive to movement of the analog mechanical linkage. The carrier is stopped anywhere within a continuum of distances responsive to stopping the trigger actuator. The trigger actuator pivots in a re-set direction, which is opposite to the actuation direction. The roller clutch is held against rotation when the trigger actuator is pivoted in the actuation direction, and the roller clutch rotates when the trigger actuator is pivoted in the re-set direction.

DETAILED DESCRIPTION

Figures 1, 5:
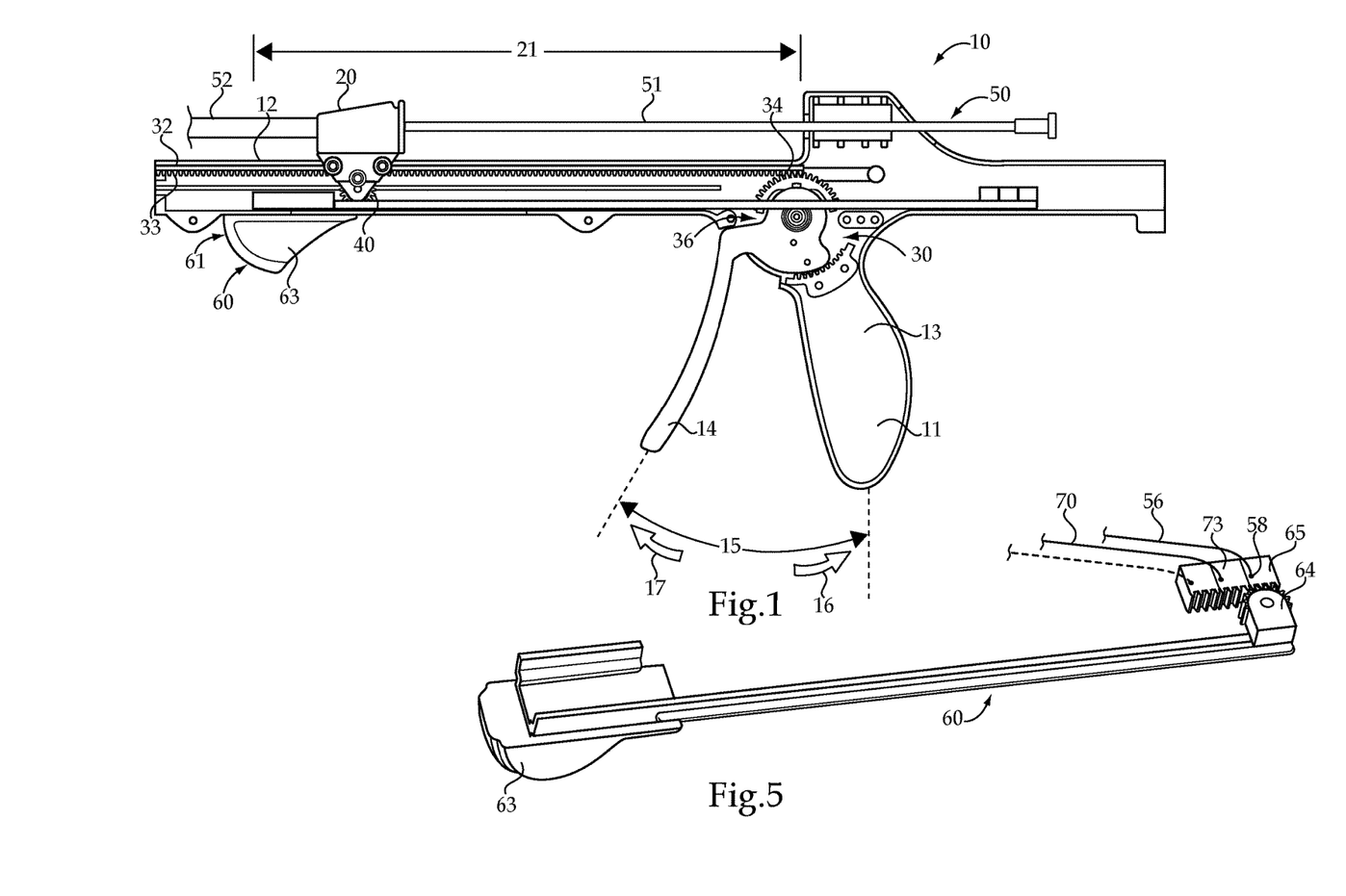
FIG. 1 is a schematic side view of a stent delivery device according to the present disclosure.
FIG. 5 is the schematic view of the secondary actuator for the stent delivery device of FIG. 1.
Figures 2, 3:
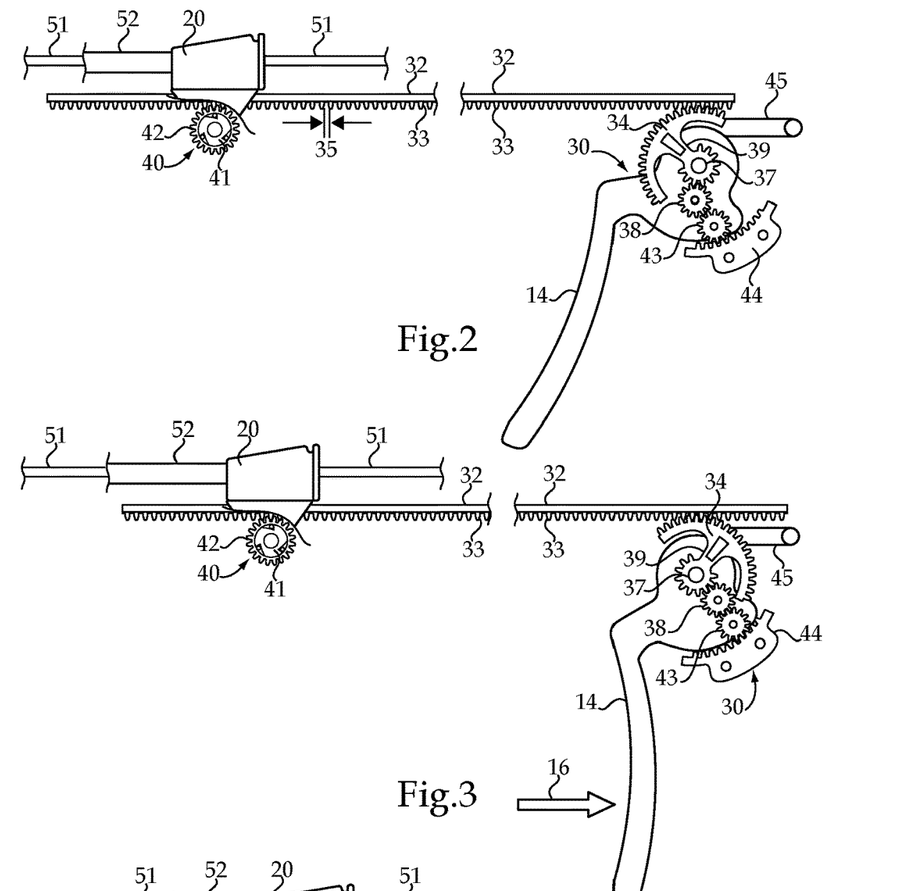
FIG. 2 is a schematic view of the planetary gear assembly and carrier portion from the stent delivery device of FIG. 1, with the trigger in the un-actuated position.
FIG. 3 is a schematic view of the planetary gear assembly and carrier portion after the trigger actuator has been moved in a actuation direction.
Figure 4:
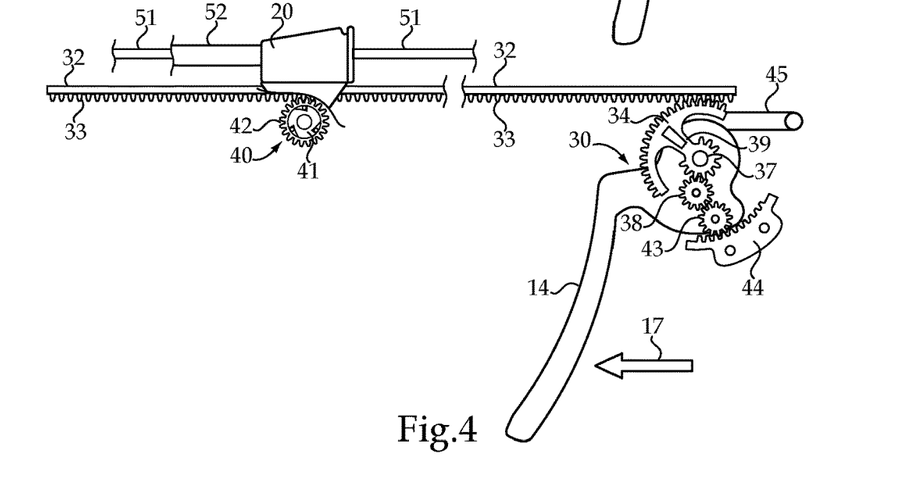
FIG. 4 is a schematic view of the planetary gear assembly and carrier portion after the trigger has been moved in the reset direction.

Referring initially to FIG. 1-4, a stent delivery device 10 includes a pistol shaped handle 11 with a barrel portion 12 extending atop a grip portion 13. A trigger actuator 14 is pivotably mounted to the pistol shaped handle 11 and defines an angle 15 with respect to the grip portion 13. A carrier 20 is slidably mounted to the barrel portion 12 of the pistol shaped handle 11. Carrier 20 may be connected to a retractable sheath 52 of a catheter assembly 50. A mechanical linkage 30, which includes a roller clutch 40, interconnects the trigger actuator 14 to the carrier 20. The angle 15 is reduced responsive to pivoting the trigger actuator 14 in an actuation direction 16 toward the grip portion 13. The pistol shaped handle 11 may include a return spring 45 that biases trigger actuator 14 in the reset direction 17. Return spring 45 is shown in FIGS. 2-4 as an elastic band stretched between pins attached to the handle 11 and trigger actuator 14, respectively. The roller clutch 40 is oriented in the mechanical linkage 30 to rotate responsive to the trigger actuator 14 pivoting in the reset direction 17, but the roller clutch 40 is held against rotation responsive to the trigger actuator 14 pivoting in the actuation direction 16. Although the roller clutch 40 is shown as attached to, and moving with, carrier 20, those skilled in the art will appreciate that the roller clutch 40 could be operably positioned elsewhere in the mechanical linkage 30 without departing from this disclosure.

In the illustrated embodiment, the mechanical linkage 30 may be an analog mechanical linkage such that the roller clutch 40 is not a ratchet. In the event that the mechanical linkage was digital, corresponding to roller clutch 40 being replaced by a ratchet, the carrier would only be able to move in increments associated with an integer number of teeth spacings 35 (FIG. 2). However, in the illustrated embodiment, roller clutch 40 may include a cam 41 positioned in a gear housing 42 (FIG. 2). Thus, in the case of an analog mechanical linkage 30, the carrier 20 is slidable and stoppable at any point in a continuum of distances 21 along the barrel portion 12. The carrier moves in proportion to a reduction of the angle 15 when the trigger actuator 14 is pivoted in the actuation direction 16.

The mechanical linkage 30 may include a rack 32 with teeth 33 meshed with a pinion 34. The continuum of distances 21 includes movement distances that are less than a teeth spacing 35 of the rack 32. As best shown in FIGS. 2-4, the teeth of gear housing 42 of roller clutch 40 are meshed with the teeth 33 of the rack 32.

The mechanical linkage 30 may include a planetary gear assembly 36 in which the pinion 34 is attached to rotate with a sun gear 37 by way of a radial connection 39. As best shown in the series of illustrations of FIGS. 2-4, the rack 32 moves fore and aft along barrel portion 12 of pistol shaped handle 11 responsive to pivoting the trigger actuator 14 in the reset direction 17 and the actuation direction 16, respectively. The trigger actuator 14 may rotate about an axis that is co-axial with sun gear 37. However, the trigger actuator 14 is attached to planetary gears 38 and 43 that are meshed with each other. In addition, planetary gear 38 is meshed with sun gear 37, and planetary gear 43 is meshed with the teeth of a partial ring gear 44 that is stationary and affixed to pistol shaped handle 11.

Figure 11:
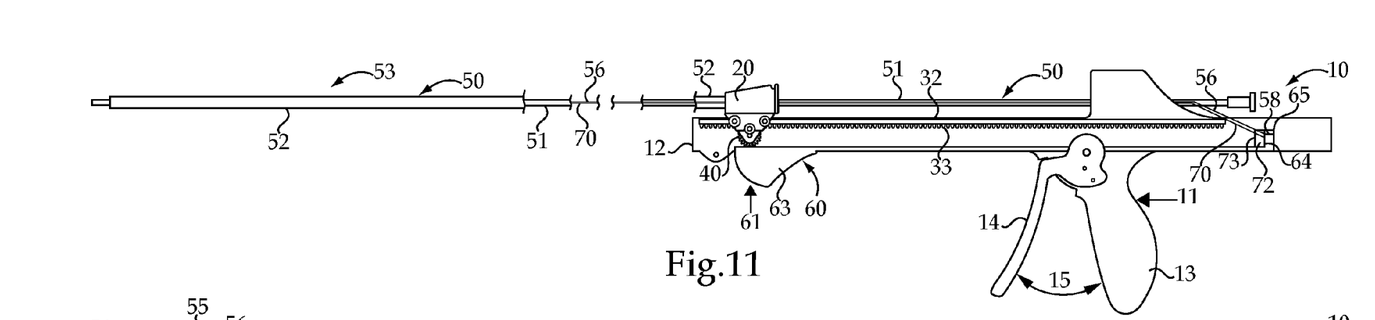
FIG. 11 is a schematic view of the stent delivery device in its pre-deployment configuration.

The catheter assembly 50, which may be a portion stent delivery device 10, includes a catheter 51 attached in a fixed position to pistol shaped handle 11. A retractable sheath 52 is connected to move with the carrier 20 relative to the catheter 51. The retractable sheath 52 is movable from a first position 53 (FIG. 11) covering a stent 55 that is supported on catheter 51 toward a second position 54 (FIG. 14) uncovering, and out of contact with, the stent 55.

Figures 6, 7:
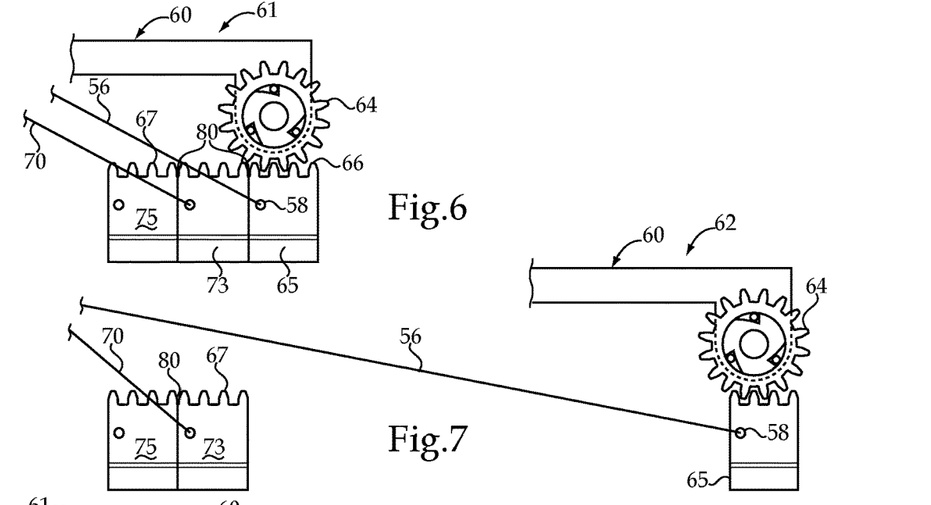
FIG. 6 is a schematic view of the portion of the secondary actuator engaged with a first rack slider, as also shown in FIG. 11.
FIG. 7 is a schematic view of the secondary actuator in its second position moving one of the rack sliders, as also shown in FIG. 15.
Figure 8:
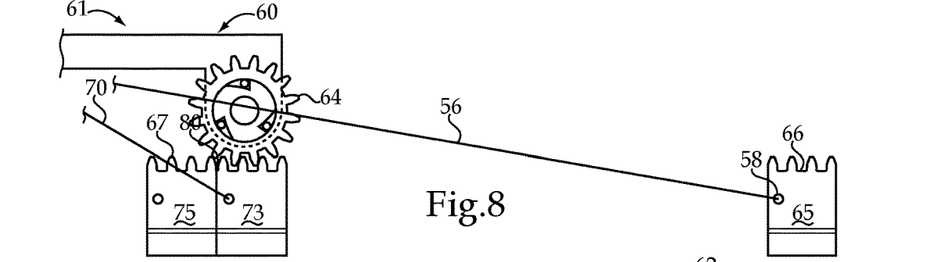
FIG. 8 is a schematic view of the secondary actuator engaged with a second rack slider, as also shown in FIG. 16.
Figure 9:
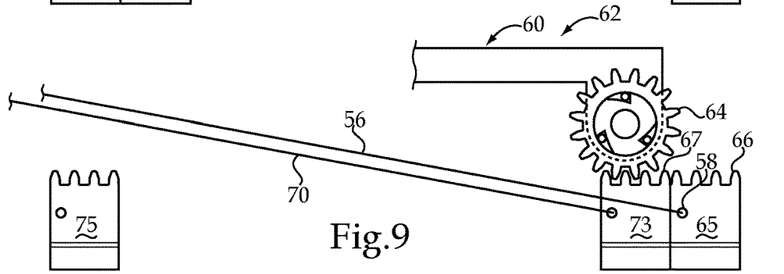
FIG. 9 is a schematic view of the secondary actuator in a second position after moving the second rack slider, as also shown in FIG. 17.
Figure 10:
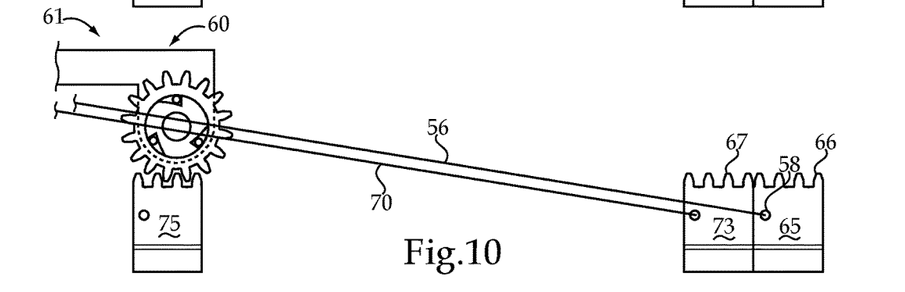
FIG. 10 is a schematic view showing the secondary actuator return to its first position and engaging a third rack slider.
Figure 14:
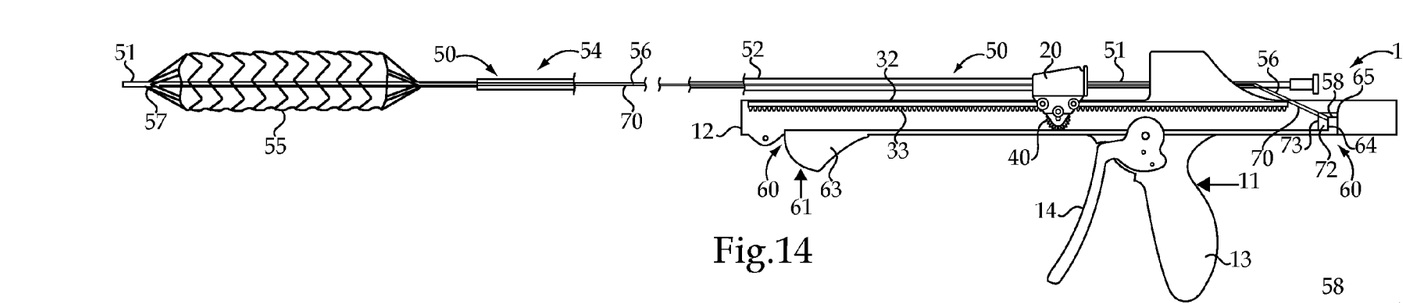
FIG. 14 is a schematic view of the stent delivery device with the retractable sheath moved to its second position.
Figure 15:
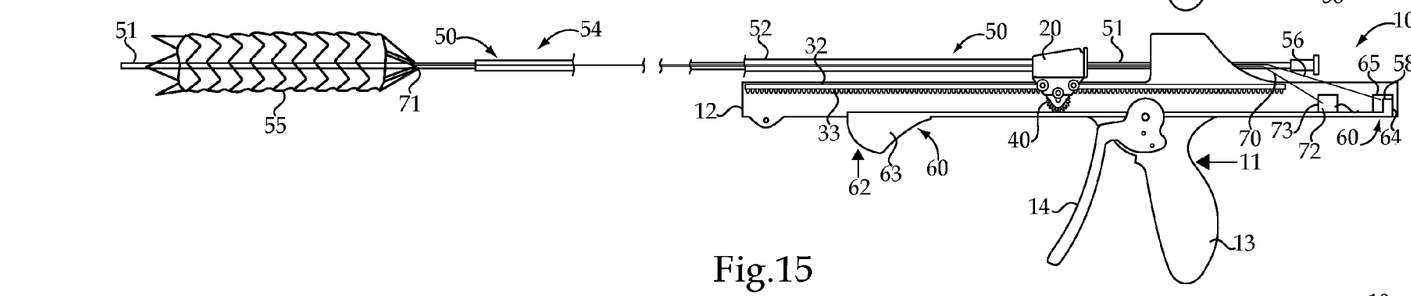
FIG. 15 is a schematic view showing a first control wire releasing the distal end of a stent.

Although not necessary and referring in addition to FIGS. 5-10, the stent delivery device 10 may be equipped with a secondary actuator 60 in the event that the catheter assembly 50 includes one or more control wires to perform various functions during the deployment of stent 55. In the illustrated embodiment, secondary actuator 60 is mounted to slide along the underside of barrel portion 12 between a first position 61 (FIG. 14) and a second position 62 (FIG. 15) to move a control wire (e.g., control wire 56). In particular, the secondary actuator 60 may include a secondary handle 63 that moves along a line parallel to barrel portion 12 from the first position 61 to the second position 62. The secondary actuator 60 may also include a clutched gear 64 that is remote from, but attached to move with, the secondary handle 63. Clutched gear 64 may be identical to the roller clutch 40 discussed earlier with regard to mechanical linkage 30, or may take the form of a ratchet without departing from the intended scope of the present disclosure. FIG. 5 shows the secondary actuator 60 separated from pistol shaped handle 11, and the series of illustrations of FIGS. 6-10 show the action of the secondary actuator 60 with several rack sliders 65, 73 and 75. In the illustrated embodiment, a first control wire 56 may have one end 57 coupled to stent 55, such as for holding the one end of the stent 55 in close proximity to catheter 51. A second end 58 of control wire 56 may be attached to move with a rack slider 65 of secondary actuator 60. Thus, when second actuator 60 moves rack slider 65 from the first position shown in FIG. 6 (and FIG. 11) to its second position shown in FIG. 7 (and FIG. 15), control wire 56 moves to release the one end of stent 55 as shown in FIGS. 14 and 15. Each of the rack sliders 65, 73 and 75 include teeth meshed with the teeth of clutched gear 64, which like roller gear 40 discussed earlier, only rotates in one direction. The teeth 66 of rack slider 65 and the teeth 67 of rack slider 73 may be configured to create a gear tooth interference stop 80 that prevents clutched gear 64 from rotating past rack slider 65 or the further most rack slider. The gear tooth interference stop 80 is created when any pair of rack sliders 65, 73 and 75 are abutting each other as shown in FIG. 6, for instance. In the illustrated embodiment, a secondary rack slider 73 is used in conjunction with a second control wire 70. In particular, one end 71 of the second control wire 70 may be coupled to stent 55, such as for holding the opposite end of the stent 55 in close proximity to catheter 51 during the deployment procedure. An opposite end 72 of the control wire 70 is connected to move with rack slider 73 under the action of secondary actuator 60 as illustrated in FIGS. 9-10 and 16-17.

Those skilled in the art will appreciate that the trigger actuator 14, the mechanical linkage 30 and the carrier 20 are responsible for taking human input and transferring it to a linear force needed to un-sheath a stent for deployment. In the illustrated embodiment, the planetary gear assembly 36 is sometimes known as a reversing planetary gear set which takes the rotation of the trigger actuator 14 and converts it to linear motion by way of the gears 34, 37, 38, 40, 43, 44 and rack 32 of the mechanical linkage 30. The gear rack 32 is coupled with the carrier 20 via a roller clutch 40 as described previously. The trigger actuator 14 is moved in the actuation direction 16 by the user and is moved back to its original position via a reset direction 17 by a return spring 45. Each pull of the trigger actuator 14 retracts the carrier 20 and hence the retractable sheath 52 a limited distance that is governed, by among other things, the angular displacement of the sun gear 37, the angular displacement of the planetary gears 38 and 43, the number of teeth on the sun gear 37 and the number of teeth on the ring gear 44. Those skilled in the art will appreciate that with appropriate design, one can engineer the relationship between how far the carrier 20 moves with each full pivoting action of trigger actuator 14. For instance, in the illustrated embodiment, one full pivoting of the trigger actuator 40 may yield about 40 millimeters of displacement for the gear rack 32 and carrier 20. Thus, for 120 millimeter stent graft, the total number of trigger pulls may be three or more. The roller clutch 40 on the carrier 20 allows for cyclical motion of the rack 32. When the trigger actuator 14 is squeezed and the gear rack 32 is pulled, the roller clutch 40 locks and pulls the carrier 20 with the rack 32. When the trigger actuator 14 is pushed back toward its original position in the reset direction 17 by the return spring 45, the rack 32 moves forward to its original position because the roller clutch allows the gear housing 42 to spin in place, leaving its longitudinal position unchanged.

INDUSTRIAL APPLICABILITY

The present disclosure finds general applicability to delivery systems for self expanding stents. The present disclosure finds specific applicability to converting a conventional two handed pin and pull stent deployment system into a single hand operation using a pistol grip. The present disclosure also finds specific applicability to stent delivery devices with the ability to move and stop the retractable sheath anywhere in a continuum of movement distances with precise control, while maintaining the built up tension in the system.

Those skilled in the art will appreciate that if the stent delivery system 10 includes a mechanical linkage 30 that includes a planetary gear assembly, the proportionality of how far carrier 20 moves responsive to each movement of trigger actuator 14 can be engineered to provide a mechanical advantage. In addition, one could expect that the trigger actuator 14 may have to be moved between one and multiple times in the actuation direction 16 to completely uncover a stent 55 depending upon a specific application. The stent delivery device 10 may be equipped with a feature that prevents secondary actuator 60 from moving away from its first position 61 until after the carrier 20 has been moved sufficiently far to completely uncover stent 55.

One major clinical advantage of the presently disclosed stent delivery device over currently available pin and pull systems is the stability, hand positioning and visual reference available in a pistol-grip style delivery system. With the stent delivery device 10 of the present disclosure, sheath 52 retraction can be performed with one hand while maintaining system stability. Another major advantage may be the ability of the practitioner to maintain hand position during tracking, placement and deployment, thus increasing the accuracy of placement and system usability.

Figure 12:
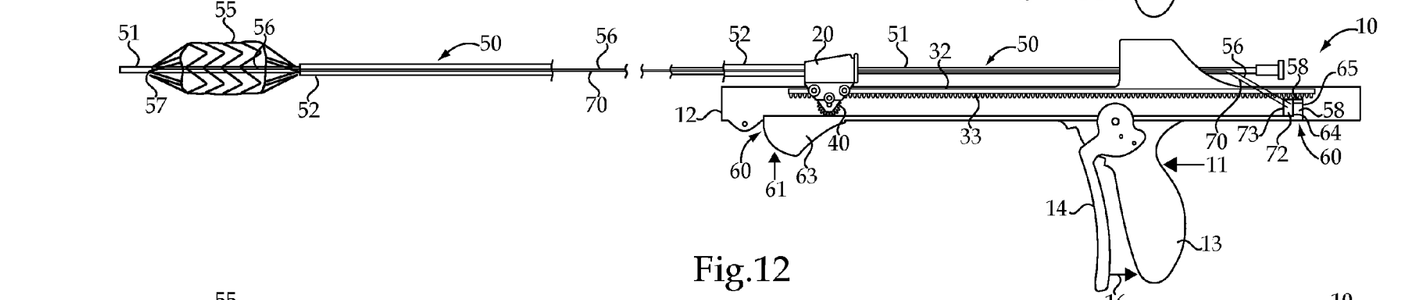
FIG. 12 is a schematic view of the stent delivery device with the retractable sheath partially retracted and the trigger actuator pivoted in an actuation direction.
Figure 13:
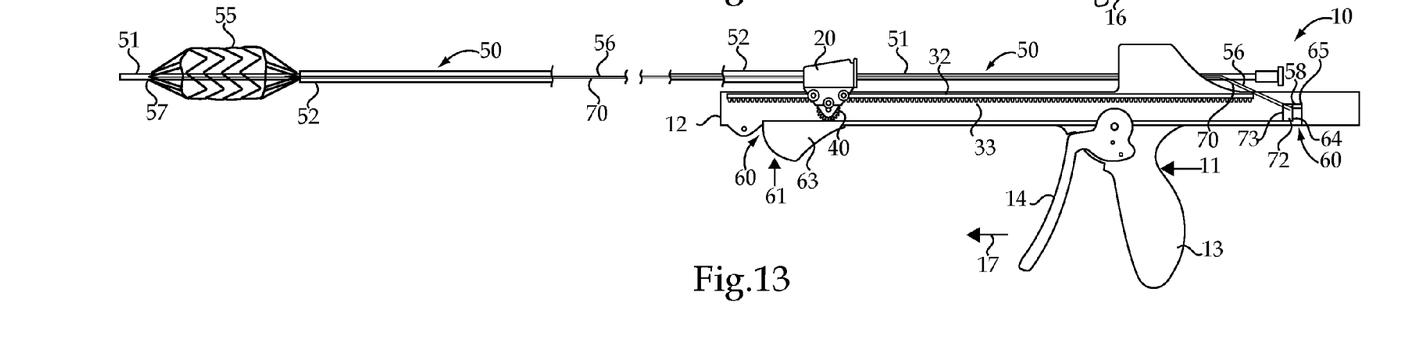
FIG. 13 is similar to FIG. 12 except with the trigger actuator pivoted in a reset direction back to its original position.
Figure 16:
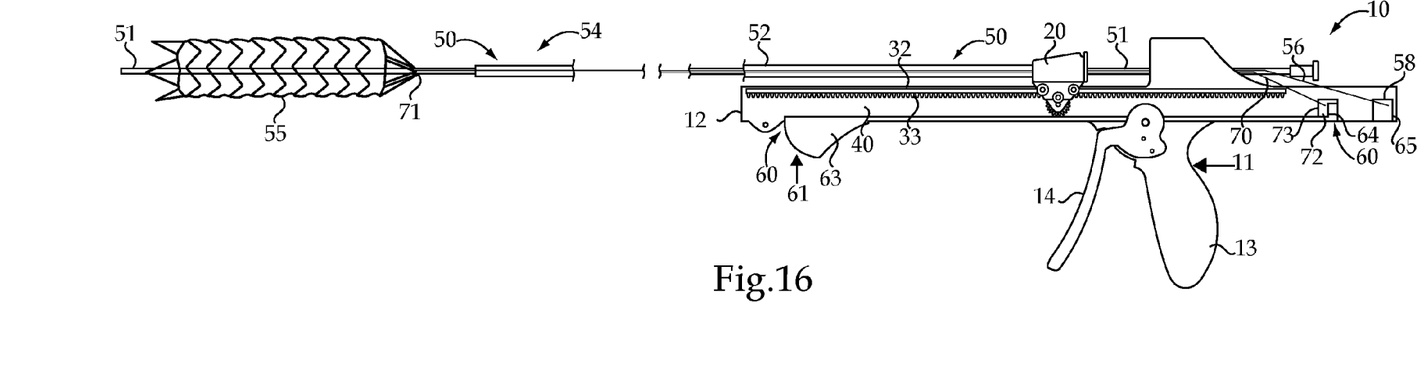
FIG. 16 is a schematic view showing the secondary actuator returned to its original position.
Figure 17:
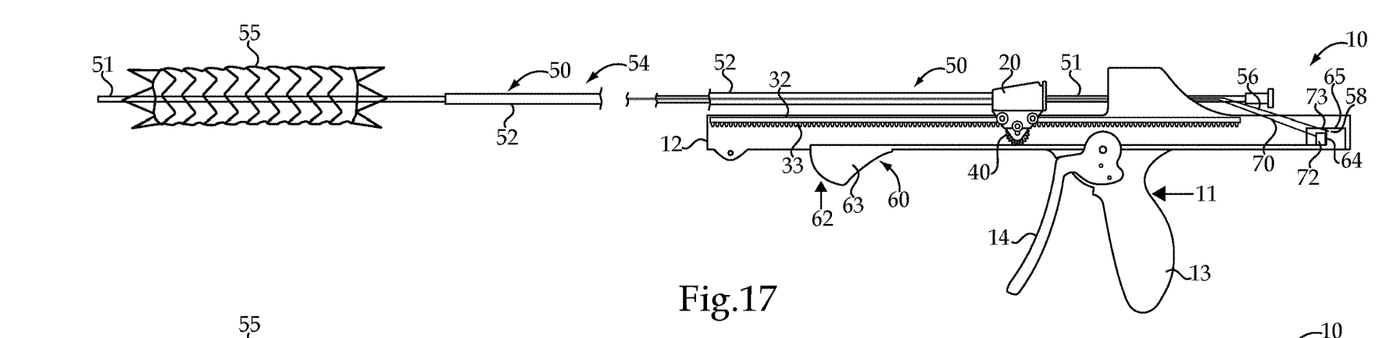
FIG. 17 is a schematic view showing the secondary actuator moving a second control wire to release the proximal end of the stent.
Figure 18:
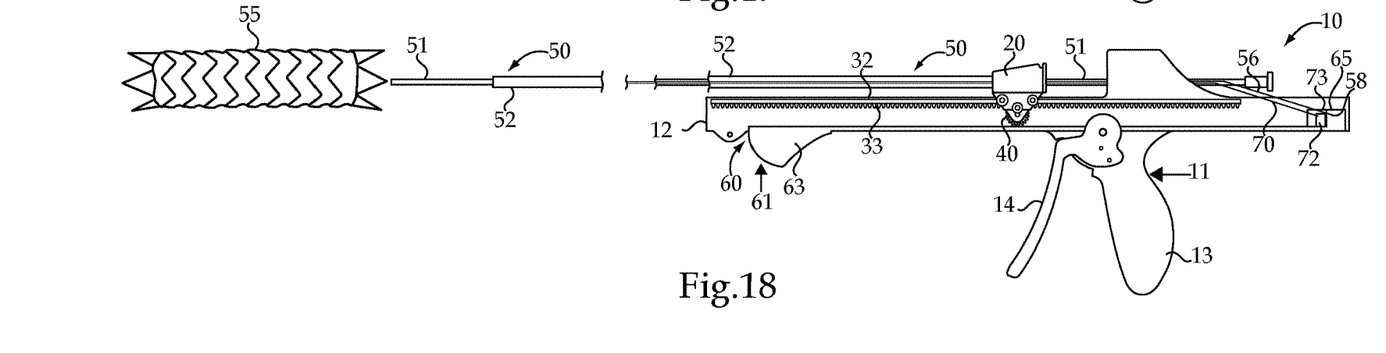
FIG. 18 is a schematic view showing the stent delivery device moving away from an implanted stent.

Referring now to FIGS. 11-18, an example sequence shows how the stent delivery device 10 may be operated to deliver a stent 55 to a desired location. FIG. 14 shows stent delivery device 10 in a pre-deployment configuration with carrier 20 positioned toward the remote end of barrel portion 12 of pistol shape handle 11 and with retractable sheath 50 in its first position 53 covering a stent 55, which is not visible in FIG. 11. The secondary actuator 60 is shown in its first position, with control wires 56 and 70 not yet in play. When the distal end of the catheter 51 is properly positioned such that the stent 55 will be deployed at a desired location, the clinician may move trigger actuator 14 in the actuation direction 16 as shown in FIG. 15 to move rack 32 backward along barrel portion 12. When this occurs, the inability of roller clutch 40 to rotate causes carrier 20 to be moved with the rack 32, causing retractable sheath 52 to move toward the pistol shaped handle 11 along the axis of the catheter assembly 50. After one full actuation of trigger actuator 14, the stent 55 may only be partially deployed as shown in FIGS. 12 and 13. After the trigger is actuated, an internal spring bias 45 moves the trigger actuator 14 in the reset direction 17 as shown in FIG. 13. After several more pivoting movements of trigger actuator 14 in the actuation direction 16 and then back in the reset direction 17, the retractable sheath 50 may be moved to its second position 54 as shown in FIG. 14 completely uncovering stent 55. In cases where the stent 55 and the delivery operation does not include any extra control wires or the like, the procedure for implanting the stent 55 could be completed at this point. However, in the illustrated embodiment, a first control wire 56 is used for releasing the remote end of stent 55 and a second control wire 70 is used for releasing the near end of stent 55 using the secondary actuator 60. In FIG. 15, the secondary actuator 60 is moved along barrel portion 12 from the first position 61 to the second position 62 to pull control wire 56 in the direction away from stent 55 to release the remote end of the stent 55 as shown in FIG. 15. Next, the secondary actuator 60 is moved back to the first position to pick up the second rack slider 73 to operate second control wire 70. This aspect is shown in FIG. 16. Next, the secondary actuator 60 again is moved from its first position 61 to its second position 62 shown in FIG. 17 to move the second rack slider 73 to pull control wire 70 to release the proximal end of stent 55 as shown in FIG. 17. At this point, the stent 55 is completely deployed and the stent delivery device 10 may be moved away from stent 55 as shown in FIG. 18.

The operation of stent delivery device 10 may include pivoting the trigger actuator 14 of the pistol shaped handle 11 toward the grip portion 13 in the actuation direction 16 one or more times to fully retract the sheath 50 to uncover stent 55. When the trigger actuator 14 is pivoted, an analog mechanical linkage 30 facilitated by roller clutch 40 interconnects the trigger actuator 14 to the carrier 20 by using the roller clutch 40. The carrier 20 may be slid along barrel portion 12 responsive to movement of the analog linkage mechanical linkage 30 and stop the carrier 20 anywhere within the continuum of distances 21 (FIG. 1) responsive to stopping the trigger actuator 14. After each actuation of trigger actuator 14, the trigger actuator may be pivoted in the reset direction 17, which is a direction opposite to actuation direction 16. During stent deployment, the roller clutch 40 is held against rotation when the trigger actuator 14 is pivoted in the actuation direction 16 so as to move with rack 32, but the roller clutch rotates when the trigger actuator 14 is pivoted in the reset direction 17.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A stent delivery device comprising:
   a pistol shaped handle with a barrel portion extending atop a grip portion;
   a trigger actuator pivotably mounted to the pistol shaped handle and defining an angle with respect to the grip portion;
   a carrier slidably mounted to the barrel portion of the pistol shaped handle;
   a mechanical linkage, which includes a roller clutch, interconnecting the trigger actuator to the carrier;
   wherein the angle is reduced responsive to pivoting the trigger actuator in an actuation direction toward the grip portion, and the angle is increased responsive to pivoting the trigger actuator in a reset direction;
   wherein the roller clutch is oriented in the mechanical linkage to rotate responsive to the trigger pivoting in the reset direction, but the roller clutch holding against rotation responsive to pivoting the trigger in the actuation direction.

2. The stent delivery device of claim 1 wherein the mechanical linkage is an analog mechanical linkage; and
the carrier is slidable a continuum of distances along the barrel portion proportional to a reduction of the angle when the trigger actuator is pivoted in the actuation direction.

3. The stent delivery device of claim 2 wherein the mechanical linkage includes a rack with teeth meshed with a pinion; and
the continuum of distances include a distance that is less than a teeth spacing of the rack.

4. The stent delivery device of claim 3 wherein the mechanical linkage includes a planetary gear assembly in which the pinion is attached to rotate with a sun gear, and the trigger actuator is attached to a planetary gear that is meshed with the sun gear.

5. The stent delivery device of claim 4 wherein the roller clutch includes a cam positioned in a gear housing that is meshed with the rack, and the carrier is attached to the cam.

6. The stent delivery device of claim 1 wherein the roller clutch includes a cam positioned in a gear housing that is meshed with the rack, and the carrier is attached to the cam.

7. The stent delivery device of claim 6 wherein the mechanical linkage is an analog mechanical linkage; and
the carrier is slidable a continuum of distances along the barrel portion proportional to a reduction of the angle when the trigger actuator is pivoted in the actuation direction.

8. The stent delivery device of claim 6 wherein the mechanical linkage includes a rack that moves for and aft along the barrel portion responsive to pivoting of the trigger actuator in the reset and actuation directions, respectively.

9. The stent delivery device of claim 1 including a catheter assembly that includes a catheter attached to pistol shaped handle and a retractable sheath connected to move with the carrier relative to the catheter; and
the retractable sheath being movable from a first position covering a stent supported on the catheter toward a second position uncovering, and out of contact with, the stent.

10. The stent delivery device of claim 9 wherein the catheter assembly includes a control wire;
a secondary actuator mounted to, and moveable with respect to, the pistol shaped handle from a first position to a second position;
one end of the control wire being coupled to the stent, and an opposite end being connected to move with the secondary actuator.

11. The stent delivery device of claim 10 wherein the secondary actuator includes a secondary handle that moves along a line parallel to the barrel portion form the first position to the second position;
the secondary actuator also includes a clutched gear attached to move with the secondary handle; and
the secondary actuator includes a rack slider connected to the opposite end of the control wire and including teeth meshed with teeth of the clutched gear.

12. The stent delivery device of claim 11 wherein the control wire is a first control wire, and the rack slider is a first rack slider;
a second control wire having one end coupled to the stent, and an opposite end connected to move with a second rack slider that has a position abutting the first rack slider.

13. The stent delivery device of claim 12 wherein the first and second rack sliders are shaped to produce a gear tooth interference stop relative to the clutched gear when abutting each other.

14. The stent delivery device of claim 1 including a secondary actuator mounted to, and moveable with respect to, the pistol shaped handle from a first position to a second position;
the secondary actuator includes a clutched gear attached to move with a secondary handle; and
the secondary actuator includes a plurality of rack sliders slidably mounted on the pistol shaped handle; and
one of the rack sliders has teeth meshed with teeth of the clutched gear.

15. The stent delivery device of claim 14 wherein the plurality of rack sliders include a first rack slider and a second rack slider that are shaped to produce a gear tooth interference stop relative to the clutched gear when abutting each other.

16. The stent delivery device of claim 14 wherein the mechanical linkage is an analog mechanical linkage; and
the carrier is slidable a continuum of distances along the barrel portion proportional to a reduction of the angle when the trigger actuator is pivoted in the actuation direction.

17. The stent delivery device of claim 16 wherein the mechanical linkage includes a rack with teeth meshed with a pinion; and
the continuum of distances includes a distance that is less than a teeth spacing of the rack.

18. The stent delivery device of claim 17 wherein the mechanical linkage includes a planetary gear assembly in which the pinion is attached to rotate with a sun gear, and the trigger is attached to a planetary gear that is meshed with the sun gear.

19. The stent delivery device of claim 18 wherein the roller clutch includes a cam positioned in a gear housing that is meshed with the rack, and the carrier is attached to the cam.

20. A method of operating a stent delivery device that includes a pistol shaped handle with a barrel portion extending atop a grip portion; a trigger actuator pivotably mounted to the pistol shaped handle and defining an angle with respect to the grip portion; a carrier slidably mounted to the barrel portion of the pistol shaped handle; an analog mechanical linkage, which includes a roller clutch, interconnecting the trigger actuator to the carrier; wherein the angle is reduced responsive to pivoting the trigger actuator in an actuation direction toward the grip portion, and the angle is increased responsive to pivoting the trigger actuator in a reset direction; wherein the roller clutch is oriented in the mechanical linkage to rotate responsive to the trigger pivoting in the reset direction, but the roller clutch holding against rotation responsive to pivoting the trigger in the actuation direction, and the method comprising the steps of:
pivoting the trigger actuator of the pistol shaped handle toward the grip portion in the actuation direction;
moving the analog mechanical linkage that interconnects the trigger actuator to the carrier responsive to pivoting the trigger actuator, and wherein the analog mechanical linkage includes the roller clutch;
sliding the carrier along the barrel portion of the pistol shaped handle responsive to movement of the analog mechanical linkage;
stopping the carrier anywhere within a continuum of distances responsive to stopping the trigger actuator;

pivoting the trigger actuator in a reset direction, which is opposite to the actuation direction; and holding the roller clutch against rotation when the trigger actuator is pivoted in the actuation direction, and rotating the roller clutch when the trigger actuator is pivoted in the reset direction.

\* \* \* \* \*